United States Patent [19]

Han et al.

[11] Patent Number: 5,457,036
[45] Date of Patent: Oct. 10, 1995

[54] PROCESS FOR PRODUCTION OF $C_{10}$ AND/OR $C_{12}$ GAMMA-LACTONES FROM THE CORRESPONDING $C_{10}$ AND/OR $C_{12}$ CARBOXYLIC ACIDS BY MEANS OF MICROBIAL BIOTRANSFORMATION IN THE PRESENCE OF MINERAL OIL

[75] Inventors: Ohantaek Han; Sunjeong R. Han, both of Germantown, Wis.

[73] Assignee: International Flavors & Fragrances Inc., New York, N.Y.

[21] Appl. No.: 382,534

[22] Filed: Feb. 2, 1995

[51] Int. Cl.$^6$ ............................................. C12P 17/04
[52] U.S. Cl. ............................................. 435/126; 435/822
[58] Field of Search ............................................. 435/126, 822

[56] References Cited

U.S. PATENT DOCUMENTS

| | | | |
|---|---|---|---|
| 4,560,656 | 12/1985 | Farbood et al. | 435/146 |
| 4,960,597 | 10/1990 | Farbood et al. | 426/3 |
| 5,112,803 | 5/1992 | Farbood et al. | 512/11 |
| 5,219,742 | 6/1993 | Cheetham et al. | 435/126 |
| 5,274,128 | 12/1993 | Farbood et al. | 549/295 |

FOREIGN PATENT DOCUMENTS

578388A2  1/1994  European Pat. Off. ........ C12P 17/04

OTHER PUBLICATIONS

Campanelli and Cooper, *The Canadian Journal of Chemical Engineering*, vol. 67, Oct. 1989, pp. 851–855, Title: "Interfacial Viscosity and the Stability of Emulsions".

Wenninger and McEwen, *International Cosmetic Ingredient Dictionary*, Fifth Edition 1993, vol. 1, published by The Cosmetic, Toiletry and Fragrance Association, pp. 415, 416 and 417.

Primary Examiner—Herbert J. Lilling
Attorney, Agent, or Firm—Arthur L. Liberman

[57] ABSTRACT

Described is a process for producing $C_{10}$ and/or $C_{12}$ gamma-lactones from the corresponding $C_{10}$ and/or $C_{12}$ carboxylic acids by use of microorganisms of the genus Mortierella, whereby a culture of the genus Mortierella is grown in a medium containing a carbon source, nitrogen source, inorganic salts, vitamins and growth factors and wherein the carboxylic acid feed rate is controlled by the response of the dissolved oxygen level in culture medium in the presence of mineral oil (liquid white paraffin oil, U.S.P. or technical grade having a specific gravity of from 0.830 up to 0.905 at 60° F. and a viscosity of from 50 up to 400 Sayboldt Seconds at 100° F., a mixture of liquid $C_{15}$–$C_{50}$ saturated hydrocarbons).

14 Claims, 4 Drawing Sheets

FIG.1

GC PROFILE FOR EXAMPLE I.

FIG.2

GC PROFILE FOR EXAMPLE I.

FIG.3

GC PROFILE FOR EXAMPLE V.

PROCESS FOR PRODUCTION OF $C_{10}$ AND/OR $C_{12}$ GAMMA-LACTONES FROM THE CORRESPONDING $C_{10}$ AND/OR $C_{12}$ CARBOXYLIC ACIDS BY MEANS OF MICROBIAL BIOTRANSFORMATION IN THE PRESENCE OF MINERAL OIL

BACKGROUND OF THE INVENTION

Our invention relates to a biotransformation process for the production of certain lactones, specifically gamma-decalactone and gamma-dodecalactone or mixtures thereof from the corresponding $C_{10}$ and/or $C_{12}$ alkanoic acids or hydrolyzates of vegetable oils containing said $C_{10}$ and/or $C_{12}$ alkanoic acids. Since the natural sources of these lactones are very limited and the use thereof are not economical because usually small quantities exist in fruits and flowers, microbiologists have been seeking alternative ways to increase the product yield and availability of $C_{10}$ and $C_{12}$ gamma-lactones by means of exploiting various microorganisms.

Thus, considerable time and effort have been expended by microbiologists in the search for better processes for the production of lactones, per se, U.S. Pat. No. 3,076,750 discloses a method of preparing certain optically active lactones and the corresponding hydroxycarboxylic acids by microbial reduction of ketocarboxylic acids. The metabolism of ricinoleic acid by some Candida strains was investigated by Okui, et al (J.Biochemistry, 54, 536–540, 1963) who showed that gamma-hydroxydecanoic acid was an intermediate in the oxidative degradation of ricinoleic acid. However, only trace amounts of gamma-hydroxydecanoic acid were recovered from the fermentation medium due to the metabolysis of gamma-hydroxydecanoic acid upon completion of the fermentation, and the toxicity of ricinoleic acid to the microorganism, which limits the amount of substrate that can be used.

U.S. Pat. No. 4,560,656 provided a method of producing optically active gamma-hydroxydecanoic acid comprising culturing or incubating a microorganism capable of hydrolyzing castor oil, and effecting beta-oxidation of the resulting hydrolysate in the presence of castor oil, to produce gamma-hydroxydecanoic acid.

U.S. Pat. No. 4,560,656 also provided a method of producing optically active gamma-hydroxydecanoic acid comprising enzymatically hydrolyzing castor oil using lipase to form an enzymatic hydrolysate and culturing or incubating a microorganism capable of effecting beta-oxidation of the enzymatic hydrolysate in the presence of said hydrolysate to produce gamma-hydroxydecanoic acid.

U.S. Pat. No. 4,560,656 also provided a method of producing optically active gamma-hydroxydecanoic acid comprising culturing or incubating a microorganism capable of hydrolyzing castor oil and a microorganism capable of effecting beta-oxidation of castor oil hydrolysate in the presence of castor oil to produce gamma-hydroxydecanoic acid.

European Published Patent Application 258,993, published on Apr. 9, 1988, discloses a process for the production of optically active gamma-hydroxydecanoic acid suitable for conversion to optically active gamma-decalactone. The process covers the steps of:

(a) culturing sporobolomyces odorous; and/or *rhodotorula glutinis* on a medium containing a ricinoleic acid source at 15°–35° C. at a pH of 3–9; and (b) lactonizing the resulting gamma-hydroxydecanoic acid to gamma-decalactone.

U.S. Pat. No. 5,274,128 (Farbood, et al, I) describes a process for the production of gamma-octalactone which exploits the ability of selected strains from the genera Mortierella, Syncephalastrum and Choanephora to transform caprylic acid or the ethyl ester of caprylic acid to octalactone according to the reactions:

and

The feeding of the octanoic acid substrate to produce gamma-octalactone using the process of the instant disclosure gives rise to a very low product yield mainly due to an insensitive dissolved oxygen response as the substrate is fed, indicating that the present invention is specific for gamma-decalactone and gamma-dodecalactone production from the respective $C_{10}$ and $C_{12}$ alkanoic acids.

U.S. Pat. No. 4,960,597 (Farbood, et al, II) issued on Oct. 2, 1990 describes fermentative production of both saturated and unsaturated lactones including the saturated gamma-decalactone from castor oil or ricinoleic acid using a microorganism such as *Candida petrophilum*, *Candida oleophila*, Candida sp. and *Candida sake* according to the reactions:

wherein Y represents an oxo-saturated, oxo-unsaturated or diunsaturated $C_9$, $C_{11}$ or $C_{13}$ moiety and wherein the number of carbon atoms in X and R are the number of carbon atoms in the Y moiety minus 1.

European Published Patent Application No. 578,338 filed on Jun. 14, 1993 (Farbood, et al, III) describes the fermentation process for preparing 10-hydroxy-$C_{18}$-carboxylic acid and gamma-dodecalactone according to the reaction sequence:

Furthermore, Campanelli and Cooper, THE CANADIAN JOURNAL OF CHEMICAL ENGINEERING, Volume 67, October 1989, pages 851–855 (Title: "Interfacial Viscosity and the Stability of Emulsions") discloses a study of a mineral oil-water-emulsifier system and discloses the effect on interfacial viscosity of the bioemulsifier produced by the yeast *Torulopsis petrophilum*.

Although the prior art describes the production of lactones from various substrate sources, nothing in the prior art discloses any biotransformation process that produces high concentrations or high yields of gamma-decalactone and gamma-dodecalactone from the corresponding $C_{10}$ and $C_{12}$ alkanoic acids wherein the feed rates are controlled by the response of dissolved oxygen tension in the presence of mineral oil as set forth in the instant disclosure.

SUMMARY OF THE INVENTION

The present invention provides a novel process for producing gamma-decalactone and gamma-dodecalactone or mixtures thereof by means of feeding a $C_{10}$ and/or $C_{12}$ alkanoic acid substrate or mixtures thereof in a viable culture of a selected microorganism belonging to the genus Mortierella in the presence of mineral oil according to the reaction sequence:

and wherein N is an integer selected from the group consisting of 1 and 2. By the term "mineral oil" is meant a (liquid white paraffin oil, U.S.P. or technical grade having a specific gravity of from 0.830 up to 0.905 at 60° F. and a viscosity of from 50 up to 400 Sayboldt Seconds at 100° F., a mixture of liquid $C_{15}$–$C_{50}$ saturated hydrocarbons).

The control of the substrate feed is determined by the response of the dissolved oxygen level in the culture medium ("dissolved oxygen" referred to hereinafter as "DO"); for example (i) if too much of the alkanoic acid substrate is fed into the medium, the DO of culture medium increases sharply; and the feed rate must then be decreased or substrate feeding must be ceased to prevent damage to cell viability; or (ii) if there is not enough carboxylic acid substrate in the medium, the DO value decreases gradually or remains substantially constant; and the feed rate of the alkanoic acid substrate must be increased or the substrate feeding must be re-initiated. Accordingly, the substrate feed rate is changed in order to achieve optimum (maximum) conversion of the substrate to the product, simultaneously with maximum preservation of cell viability. The substrate feed may be automatically or manually carried out according to a predetermined feed schedule which may be obtained by means of analysis of the accumulated substrate feed data. The $C_{10}$ and/or $C_{12}$ carboxylic acid substrate conversion to the corresponding $C_{10}$ and/or $C_{12}$ lactone is greatly improved by the addition of "mineral oil" (liquid white paraffin oil, U.S.P. or technical grade having a specific gravity of from 0.830 up to 0.905 at 60° F. and a viscosity of from 50 up to 400 Sayboldt Seconds at 100° F., a mixture of liquid $C_{15}$–$C_{50}$ saturated hydrocarbons) during the substrate feeding period.

Mineral oil as defined, supra, was chosen for dual purposes, which are: (a) to act as the supply medium of decanoic acid and (b) to act as the extractant of the lactone(s) product from aqueous medium. Mineral oil has several important features for this particular process, including:

(i) miscibility with decanoic acid and dodecanoic acid; since the solubilities of decanoic acid and dodecanoic acid in water are much less than in oil, mineral oil can be used as an acid reservoir or buffer to prevent an accidental increase in the acid level or decrease in pH;

(ii) high solubility for the lactones; since the lactone product can be continuously stripped out from the aqueous medium and retained in the oil phase, a low level of the lactone can be maintained in the aqueous medium for a prolonged period of time which reduces end product inhibition and toxicity; and (iii) requirement of a relatively simple downstream process and possibility of recycling of oil; since the lactone and its corresponding acid are major components of the reaction product, comprising about 80–95% of total volatiles retained in the mineral oil, the present invention provides not only a much simpler downstream process, but also provides for the recycling of mineral oil after recovery of the lactone and the acid.

Examples of other "mineral oils" having a specific gravity of from 0.830 up to 0.905 at 60° F. and a viscosity of from 50 up to 400 Sayboldt Seconds at 100° F. are set forth at pages 415, 416 and 417 of the International Cosmetic Ingredient Dictionary, Fifth Edition, 1993, Volume 1, published by the Cosmetic, Toiletry and Fragrance Association of 1101 17th Street, N.W., Suite 300, Washington, D.C. 20036-4702 (Editors: Wenninger and McEwen). These mineral oils have the CAS Numbers 8012-95-1 and 8042-47-5 and the EINECS Numbers 232-384-2 and 232-455-8.

Examples of useful mineral oils are:

(i) SUPERLA® white mineral oil #5 NF of Amoco Oil Company;

(ii) SUPERLA® mineral oil #6 NF of Amoco Oil Company;

(iii) SUPERLA® white mineral oil #7 NF of Amoco Oil Company;

(iv) SUPERLA® mineral oil #35 NF of Amoco Oil Company;

(v) BRITOL® 6 of the Witco Corporation;

(vi) BRITOL® 9 of the Witco Corporation;

(vii) Carnation White Mineral Oil of the Witco Corporation;

(viii) DRAKEOL® 6 of the Penreco Corporation; and (ix) DRAKEOL® 9 of the Penreco Corporation.

The front cover page and pages 415, 416 and 417 of the International Cosmetic Ingredient Dictionary, Fifth Edition, 1993, Volume 1, published by the Cosmetic, Toiletry and Fragrance Association are incorporated by reference herein.

DETAILED DESCRIPTION OF THE INVENTION

The present invention provides a novel process for producing gamma-decalactone and gamma-dodecalactone or mixtures thereof, indicated by the generic structure:

wherein N is an integer, 1 or 2, by feeding a $C_{10}$ and/or $C_{12}$ alkanoic acid substrate or mixture thereof in a growing culture of a selected microorganism of the Mortierella genus in the presence of mineral oil (liquid white paraffin oil, U.S.P. or technical grade having a specific gravity of from 0.830 up to 0.905 at 60° F. and a viscosity of from 50 up to 400 Sayboldt Seconds at 100° F., a mixture of liquid $C_{15}$–$C_{50}$ saturated hydrocarbons) according to reaction sequence:

Other vegetable oils such as coconut oil, babassu kernel oil or palm kernel oil in the presence of lipase and their hydrolyzates may be fed into the reaction mass to produce the mixture of gamma-decalactone and gamma-dodecalactone in accordance with the present invention.

In particular, it is preferable to use decanoic acid for gamma-decalactone and dodecanoic acid for gamma-dodecalactone or a mixture of decanoic acid and dodecanoic acid for a mixed product of gamma-decalactone and gamma-dodecalactone because pure acid forms have particular advantages in the recovery and purification processes of the lactones due to minimum numbers of other contaminants in the distilled oil product.

Suitable fungal species for the process of the present invention belong to the genus Mortierella as listed below:

*Mortierella isabellina*, ATCC 44583;
*Mortierella isabellina*, ATCC 38063;
*Mortierella isabellina*, CBS 221.29;
*Mortierella isabellina*, IFO 7873;
*Mortierella isabellina*, IFO 7884; and
*Mortierella ramanniana* var. *angulispora*, IFO 81870.

*Mortierella isabellina*, IFO 7873 is a particularly preferred microorganism for the process of the present invention.

Various media formulations known to be suitable for Mortierella growth can be employed in the process of the invention, in which a suitable medium should provide at least one carbon source, a nitrogen source, inorganic salts, vitamins and growth factors. The process conditions of our invention preferably include proper controls for monitoring of the pH, temperature, agitation aeration, dissolved oxygen and substrate feed rate during the course of the process of our invention.

Suitable carbon sources consist of an organic source of carbon such as glucose, fructose, sucrose, maltose, lactose, mannitol, sorbitol, glycerol, invert sugar, molasses, corn syrup and corn syrup solids or other materials containing any of the foregoing substances. Suitable nitrogen sources include organic and inorganic nitrogen-containing substances such as peptone, yeast extract, meat extract, enzymatic digest of soy, casein, corn steep liquor, urea, amino acids, ammonium salts, nitrates and other materials containing any of the foregoing substances. Suitable inorganic salts include the phosphate and sulfate salts of magnesium, sodium, calcium and potassium. Vitamins and other growth factors can be supplemented in separate forms, in mixed forms of their complexes or in the form of a yeast extract, corn steep liquor or meat extract.

Thus the complex media in which the selected microorganisms are grown are of the conventional types which can be modified in various ways to ensure the growth of the microorganisms and to produce gamma-lactones from the corresponding alkanoic acids or hydrolyzates of vegetable oils which contain decanoic and/or dodecanoic acids, as exemplified in the Examples set forth, infra.

This invention is characterized by the controlling of the substrate feed rate by means of the use of sensitive response of dissolved oxygen tension caused by the level of acid substrate in a culture medium.

The substrate acid conversion to the corresponding lactone is greatly improved by the addition of mineral oil (liquid white paraffin oil, U.S.P. or technical grade having a specific gravity of from 0.830 up to 0.905 at 60° F. and a viscosity of from 50 up to 400 Sayboldt Seconds at 100° F., a mixture of liquid $C_{15}-C_{50}$ saturated hydrocarbons) during the substrate feed period.

The $C_{10}$ and/or $C_{12}$ carboxylic acid substrate feed rate is easily controlled by the response of the dissolved oxygen level in the culture medium; for example, if an excess of substrate is fed into the medium, the DO of culture medium increases sharply; and the acid feed rate either (i) must be decreased or (ii) acid feeding must be ceased in order to prevent cell damage. On the contrary, if there is insufficient substrate in the culture medium, the DO value decreases gradually or remains constant for a period of from about 5 minutes up to about 30 minutes; and the feed rate of carboxylic acid substrate either (i) must be increased or (ii) the substrate feeding must be initiated again in order to achieve maximum conversion of the substrate to the product (lactone) with preservation of maximum cell viability.

The carboxylic acid substrate feeding may be carried out according to a predetermined feed schedule, which is obtained from analyzing the accumulated substrate feed data.

To achieve high yield of lactones, the medium should provide sufficient nutrients for active growth of the selected Mortierella microorganisms and for biotransformation of the $C_{10}$ and/or $C_{12}$ alkanoic acids to the corresponding $C_{10}$ and/or $C_{12}$ lactones.

A selected Mortierella microorganism is inoculated into a seed culture medium and incubated to allow full growth. The seed culture provides the inoculum for the fermentor medium. The concentration of the microorganism may be in the range of from about 0.1 up to about 20% based on the working volume of the fermentor, preferably in a range of from 3 up to 10%. The fungal cultivation may proceed at a pH in the range of from about 3 up to about 9, preferably in the range of from about 4 up to about 7. The pH of the medium may be controlled by the addition of inorganic or organic acid or base such as hydrochloric acid, phosphoric acid, sulfuric acid, acetic acid, sodium hydroxide, potassium hydroxide, calcium hydroxide and ammonia. The medium temperature may be varied in the range of from about 15° C. up to about 45° C., preferably from about 27° C. up to about 35° C. for gamma-decalactone and from about 27° C. up to about 40° C. for gamma-dodecalactone production. The cultivation is carried out under aerobic conditions provided by various physical means of agitation and aeration methods. The aeration rate is in the range of from about 0.3 up to about 3.0 v/v/m (liters of air/minute/liter of fermentor contents) preferably from about 1.0 up to about 2.0 v/v/m, in order to provide enough oxygen supply for cell growth and hydroxylation reaction by the selected Mortierella microorganism. The substrate may be added either alone or in combination with mineral oil and/or another carbon source such as glucose and/or other substrate such as hydrolyzates of the above-described vegetable oils and/or vegetable oil with addition of lipase. Preferably, the substrate acid is fed at the stationary phase of growth after from about 12 up to about 30 hours of initial growth period, although it may be possible to feed the substrate at any of the growth phases.

The $C_{10}$ and $C_{12}$ carboxylic acid substrate feed rate is commenced in the range of from about 0.1 up to about 100 grams/hour/liter, preferably in the range of from about 1 up to about 5 grams/hour/liter. The carboxylic acid substrate feed rate is controlled by the response of dissolved oxygen (DO) level measured by use of a membrane electrode. The substrate feed may be automatically or manually carried out according to a predetermined feed schedule, which may be obtained by means of analyzing the accumulated substrate feed data.

The mineral oil is added at the concentration of from about 1% up to about 80% by volume of total fermentor contents volume, preferably at from about 20% up to about 50% of total fermentor contents volume. Different types of mineral oil may be used with a viscosity range of from about 50 SUS (Sayboldt Seconds at 100° F.) up to about 400 SUS, preferably with low to medium viscosities of from 50 SUS up to 200 SUS. Mineral oil is added at any phases of fungal growth, preferably after 0–5 hours of substrate feeding. Mixtures of mineral oil with lactone(s) reaction product may be exchanged with fresh mineral oil in a batch mode or a continuous mode during the biotransformation period by means of various exchange methods in order to increase the $C_{10}$ and/or $C_{12}$ lactone reaction product yield. The total carboxylic acid substrate feeding period varies depending on the specific incubation parameters, such as the strain of Mortierella microorganism employed, composition of the culture fermentor medium, fermentor conditions (pH, temperature, agitation and aeration rates), the substrate to be fed and the substrate feed rate. Generally, a 20 liter fermentor requires between 10 and 60 hours of total carboxylic acid substrate feeding period. The substrate and product (lactone) concentrations in aqueous and/or oil phase(s) can be monitored by standard analytical techniques such as GLC, HPLC, IR and NMR analyses. The biotransformation process is generally terminated when there is no net production of lactone and no consumption of the substrate or there is no longer any metabolic activity of the Mortierella microorganism. By heating the culture broth and mineral oil mixture under acidic conditions, from about 90% up to about 99% of lactone produced is extracted in the mineral oil phase. The resulting product containing the lactone is further treated to remove the contaminants and is then distilled (for example, by means of fractional distillation) using a standard product recovery process to obtain a purified gamma-lactone product.

When carrying out the process of our invention under the above ranges of reaction conditions, mixtures of optically active hydroxycarboxylic acids having the structures:

and are produced which, in turn, give rise to production of optically active lactones having the structures:

and

As a general rule, the laevorotatory isomers are predominately produced.

The resulting products have uses, interalia, for augmenting, enhancing or imparting aromas and tastes to consumable materials such as perfume compositions, perfumed articles (such as solid or liquid anionic, cationic, nonionic or zwitterionic detergents, fabric softener compositions and hair preparations), colognes, foodstuffs, chewing gums, smoking tobaccos and the like.

DETAILED DESCRIPTION OF THE DRAWINGS

Figure 1:
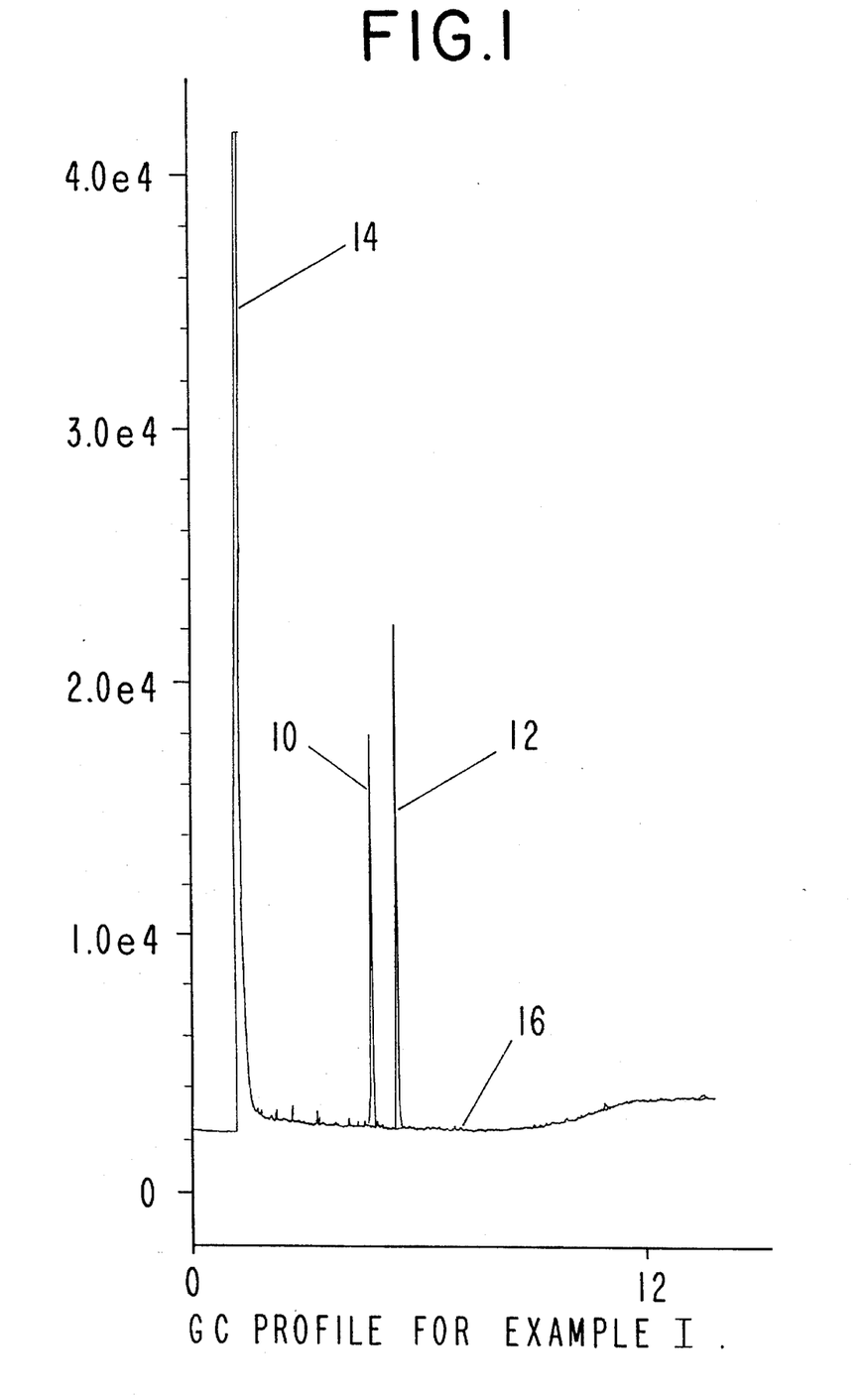
FIG. 1 is the GC profile of the reaction product of Example I containing gamma-decalactone having the structure.
Figure 2:
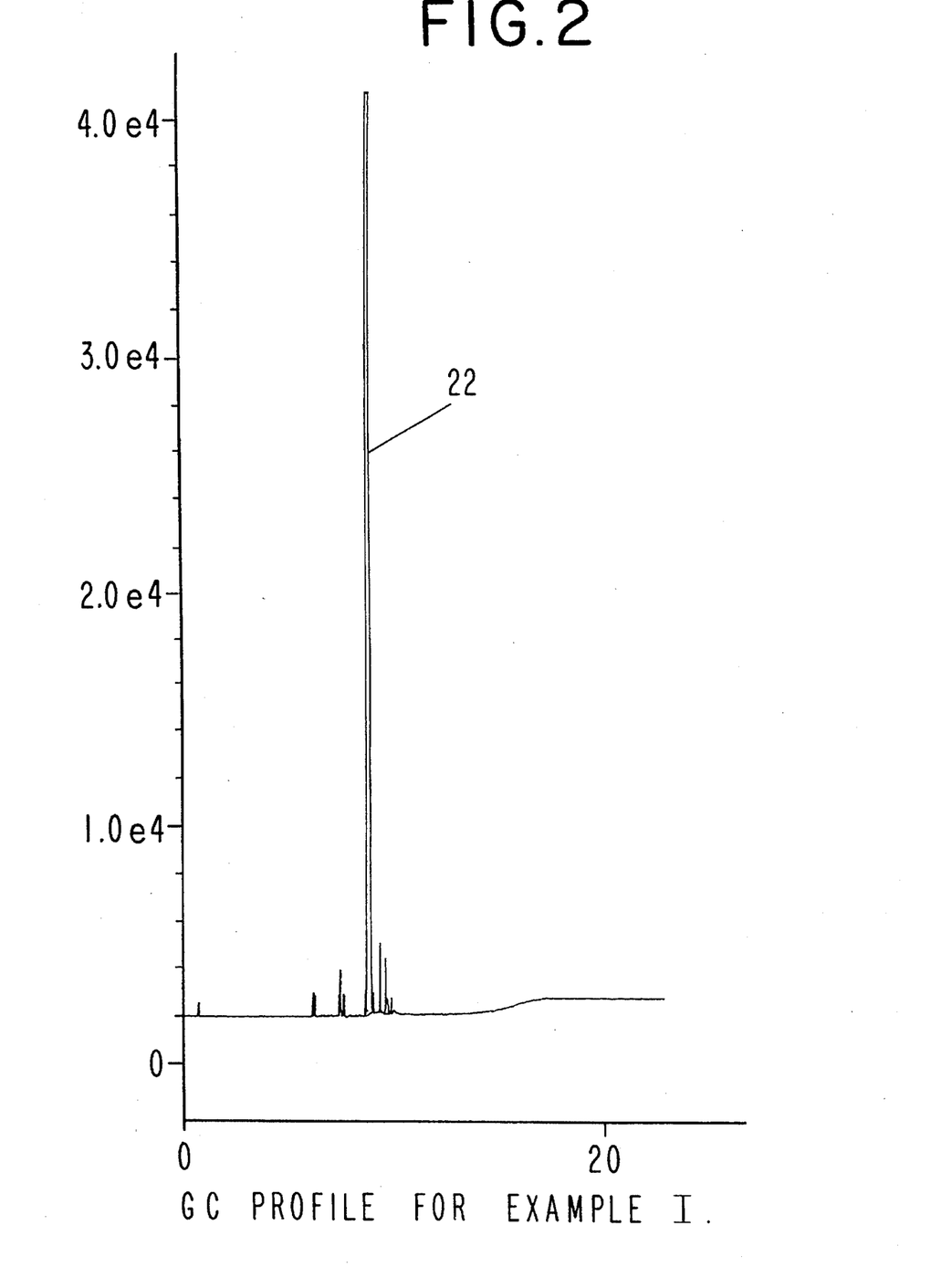
FIG. 2 is the GC profile for the purified gamma-decalactone produced according to Example I.
Figure 3:
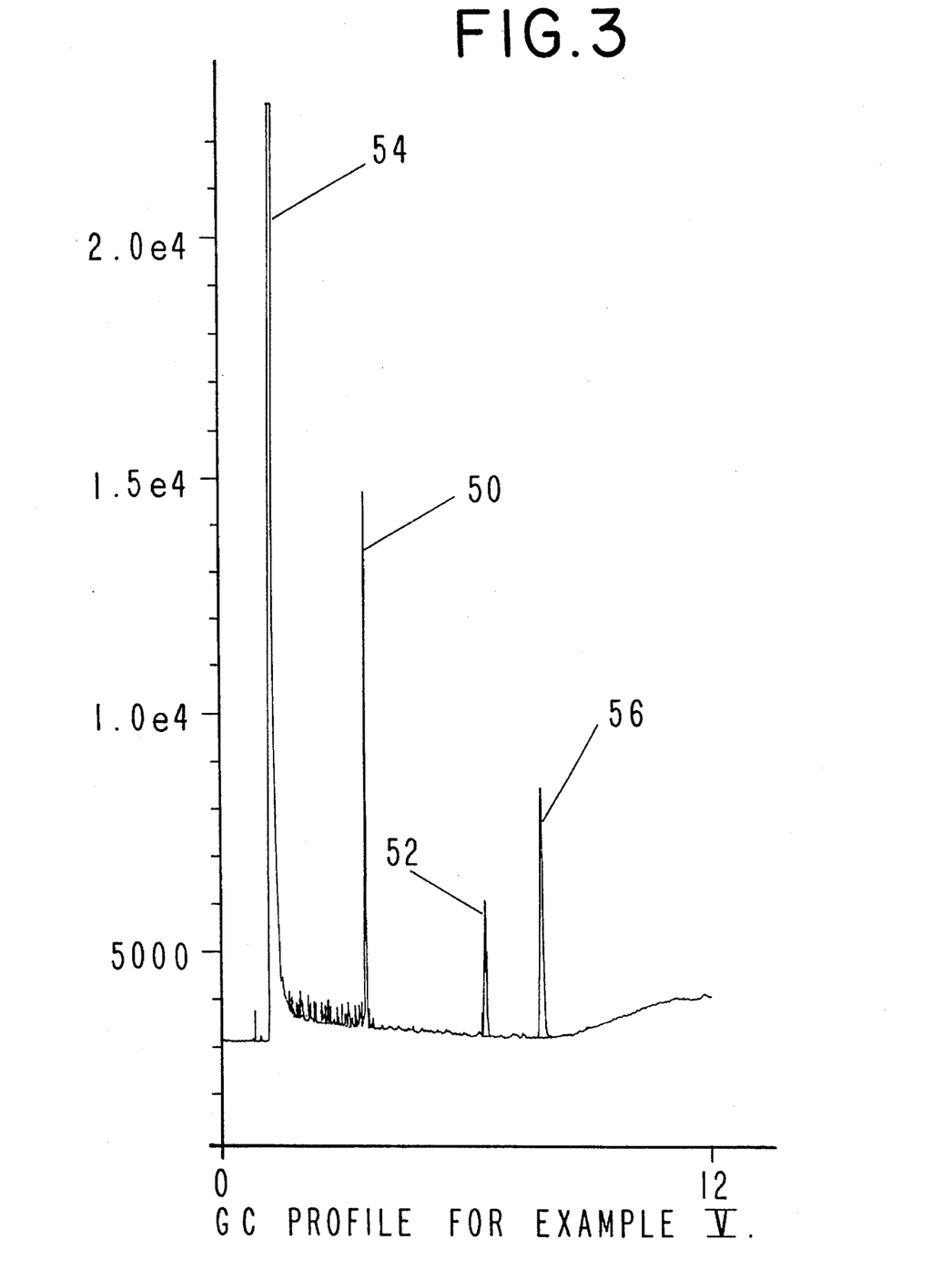
FIG. 3 is the GC profile for the reaction of Example V containing gamma-dodecalactone having the structure.
Figure 4:
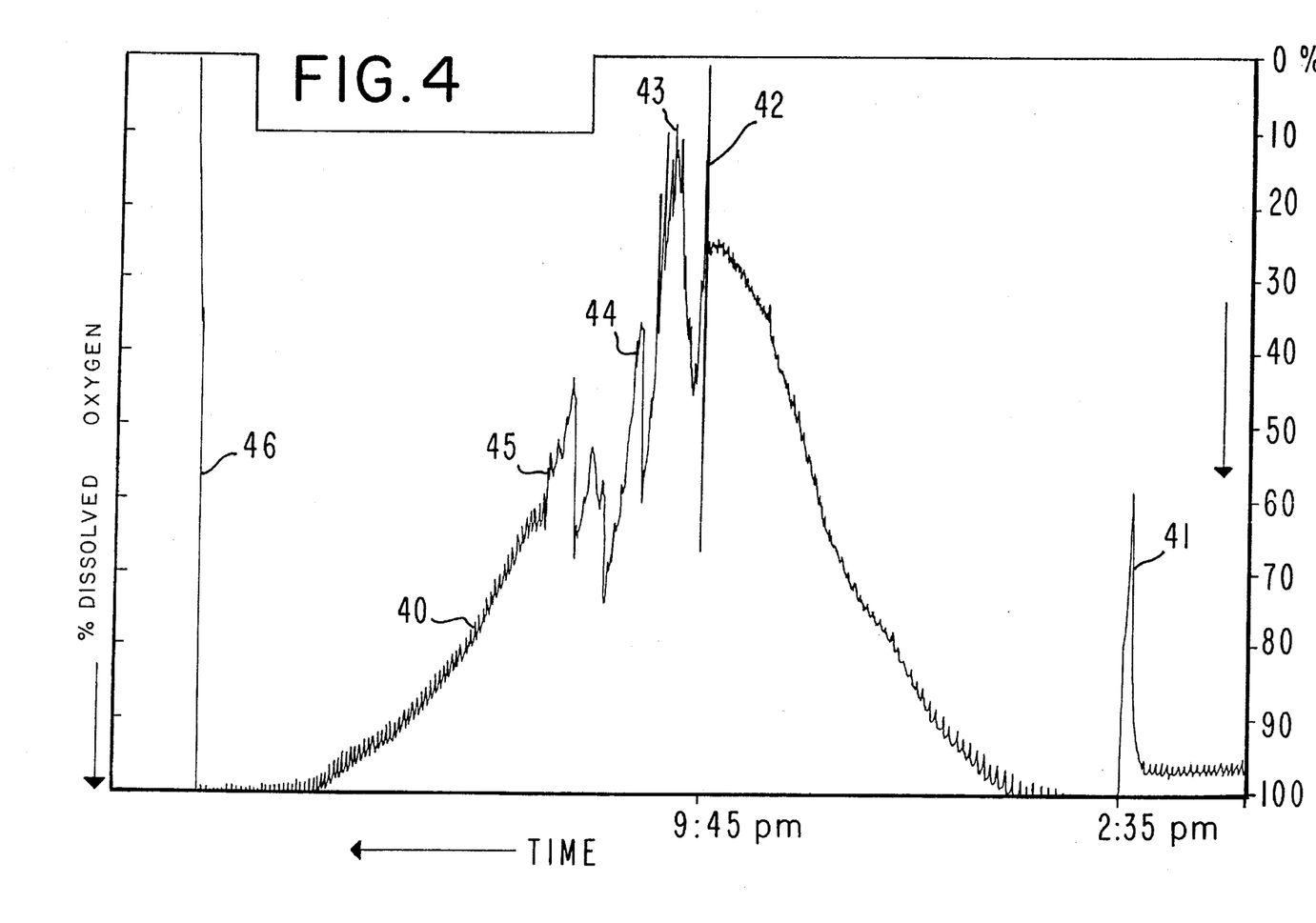
FIG. 4 is a graph showing the progression of the reaction of Example I as a function of the percentage of dissolved oxygen in the fermentor batch. The percentage of dissolved oxygen is on the "Y" axis and the time elapsed during the progression of the reaction is on the "X" axis.

Referring to FIG. 1, FIG. 1 is the GC profile for the reaction product of Example I (crude reaction product). The peak indicated by reference numeral 14 is for the mineral oil. The peak indicated by reference numeral 10 is for the delta-nonalactone having the structure:

a "internal standard" for the analysis. The peak indicated by reference numeral 12 is for the gamma-decalactone having the structure:

The peak indicated by reference numeral 16 is for unreacted decanoic acid having the structure:

Referring to FIG. 2, FIG. 2 is the GC profile for purified gamma-decalactone having the structure:

The peak indicated by reference numeral 22 is the peak for the gamma-decalactone having the structure:

Referring to FIG. 3, FIG. 3 is the GC profile for the reaction product of Example V. The peak indicated by reference numeral 54 is the peak for the mineral oil. The peak indicated by reference numeral 50 is the peak for the delta-nonalactone "internal standard". The peak indicated by reference numeral 52 is the peak for the gamma-dodecalactone having the structure:

The peak indicated by reference numeral 56 is the peak for the unreacted dodecanoic acid having the structure:

Referring to FIG. 4, FIG. 4 is a graph showing time transpired on the "X" axis versus percent of dissolved oxygen in the fermentation batch on the "Y" axis. The peak indicated by reference numeral 41 is the peak showing the change and percent of dissolved oxygen at the point of inoculation with 600 ml of inoculum. The peak indicated by reference numeral 42 is the peak showing the percent decrease (and then increase) of dissolved oxygen in the fermentation batch at the start of the feeding of the decanoic acid substrate. The peak indicated by reference numeral 43 shows the percent decrease (and then the increase) of dissolved oxygen when 1 liter of mineral oil was added to the fermentation batch. The peak indicated by reference numeral 44 shows the decrease and then the increase of percent dissolved oxygen when the agitation rate was changed and when additional mineral oil was added. The peak indicated by reference numeral 45 shows the decrease and then the increase of percent dissolved oxygen when the agitation rate and aeration rates were changed. Reference numeral 40 is the reference numeral for the graph of percent dissolved oxygen versus time. The peak indicated by reference numeral 46 is the peak showing the point where the reaction is terminated.

The following examples are given to illustrate embodiments of the invention as it is preferred to practice it. It will be understood that these examples are illustrative and the invention is not to be considered as restricted thereto except as indicated in the appended claims.

All parts, proportions, percentages and ratios hereinafter referred to are by weight unless otherwise indicated.

EXAMPLE I

Production of Gamma-decalactone in 20 Liter Fermentors

Reactions:

*Mortierella isabellina* IFO 7873 is maintained on PDA (potato dextrose agar) plates at 25° C. and subcultured by transferring 6 mm diameter discs of mycelial mat to new plates. Sterile PDA slants are also prepared in culture tubes and inoculated by streaking a loopful of spores from the 7–14 day old PDA plates. The PDA slants are incubated for 3–4 days at 30° C., then stored in a refrigerator.

The medium of seed flasks consists of bactopeptone (1.0%), yeast extract (0.5%), TWEEN® 80 (0.05%) (trademark of Imperial Chemical Industries for polyoxyethylene sorbitan monooleate) and glucose (5.0%). The medium pH is adjusted to 4.5 using 85% phosphoric acid and flasks containing 200 ml of medium are autoclaved for 30 minutes at 121° C. The inoculum of the seed flask is one PDA slant prepared above. Spores are scraped from the slant with an inoculum loop after adding about 10 ml of sterile seed medium. The seed flasks are incubated for 2–3 days at 29° C., 120 rpm. The medium of propagation flask with the above medium is inoculated with 30 ml of seed flask culture prepared above. The propagation flasks are incubated for 2–3 days at 30° C., 150 rpm.

The production medium of 20 liter fermentor consists of TASTONE® 154 (1.0%), TASTONE® 900 (0.5%) (TASTONE® is a trademark of the Red Star Division of Universal Foods, Inc. and is a primary grown yeast extract manufactured by the Red Star Division of Universal Foods, Inc. of 433 East Michigan Street, Milwaukee, Wis. 53202), TWEEN® 80 (0.05%), 10% antifoam (0.5%) (MAZU DF 100), and glucose (2.0%). Sterile 50% (w/v) glucose solution is added after sterilization of the medium. The ingredients are measured based on 12 liter working volume of the fermentor. The production medium is sterilized at 121° C. for 25 minutes. 500 Ml of sterile 50% glucose is added after sterilization. The medium pH is adjusted to 6.5 using 85% phosphoric acid. The production medium is inoculated with 600 ml of the above propagation culture. Fermentor conditions are as follows:

| pH: | no control for initial 24–28 hours; |
|---|---|
| Temperature: | 29° C.; |
| Aeration: | 2.0 v/v/m (liters air/minute/liter fermentor contents); and |
| Agitation: | 400 rpm. |

The medium pH, DO and temperature are monitored during the course of growth and biotransformation process. When the *Mortierella isabellina* IFO 7873 is fully grown after about 24 hours, the feeding of decanoic acid and mineral oil (Amoco Oil Company SUPERLA® White Mineral Oil #5:viscosity:55.5 SUS at 100° F.; specific gravity:0.85 at 60° F.; 4.:minus 12° C.; refractive index:1.466) mixture (1:9 weight:weight ratio) is initiated at a rate of 2.4 grams of decanoic acid/hour/liter which is changed by the response of dissolved oxygen (DO) measured by a membrane electrode.

In the event that the DO increases suddenly, the acid feeding is ceased but resumed feeding whenever the DO drops gradually or stays constant for a substantial period of time, e.g., 0.5 hours. Average decanoic acid feeding rate over 30 hours is 0.5 grams/hour/liter. 4 Kg of mineral oil (Amoco Oil Company SUPERLA® White Mineral Oil #5) and 20 grams of 10% antifoam (MAZU DF 100) are added when the gamma-decalactone level reaches 0.5 grams/liter. The DO change of the culture medium is monitored very closely to control the acid feed rate (as set forth in FIG. 4 described in detail in the detailed description of the Drawing Section, supra).

The glucose level is maintained at 0.5–2.0 grams/liter during the gamma-decalactone production period. When the gamma-decalactone level in the oil phase is above 10 grams/kilogram of oil phase, an additional 2.0 kg batch of mineral oil and 10 grams of 10% antifoam agent is added. The DO increases gradually as decanoic acid is fed over a period of 24 hours. Gamma-decalactone and decanoic acid levels in the oil and aqueous phases are also monitored using gas chromatography (GC) every hour to ensure that the decanoic acid level in the oil phase is maintained below 1.0 grams/kilogram. At the end of the biotransformation, the broth pH is adjusted between 2 and 4 using citric acid. 30% By weight of the batch of sodium chloride is then added to the fermentation batch. The fermentation batch is then heated to 100° C. for a period of 15 minutes. The oil layer containing most of the gamma-decalactone and decanoic acid is separated from the aqueous layer and the oil layer is collected in order to remove decanoic acid by means of the addition of base thereto. To the 6 kg of oil layer, 12 liters of water is added and the resulting mixture is stirred vigorously. The pH of the oil/water mixture resulting therefrom is then adjusted to 8.5 and heated to 80° C. to remove decanoic acid from the oil phase. The cleaned oil and gamma-decalactone mixture is then treated by means of "rushover" distillation at 225° C. and 3 mm/Hg pressure. The recovered oil distillate weighs 81.8 grams. The purity of gamma-decalactone in the crude oil distillate is 95.4%. Therefore, 78.0 grams of gamma-decalactone is recovered from the fermentor and the gamma-decalactone yield is calculated as 6.5 grams/liter of liquid medium.

EXAMPLE II

Production of Gamma-decalactone in 20 Liter Fermentors

Reactions:

The medium of seed and propagation flasks are prepared, inoculated and incubated in the same manner as set forth in Example I, supra.

12 Liters of production medium in a 20 liter fermentor consists of peptone (1.0%), yeast extract (0.5%), TWEEN® 80 (0.05%), 10% antifoam (MAZU DF 100) (0.5%) and glucose (2.0%). The ingredients are measured based on 12 liters of working volume of the fermentor. The production medium is sterilized at 121° C. for 25 minutes. 500 Ml of sterile 50% glucose is added after sterilization. The fermentor pH is adjusted to 6.5 using 85% phosphoric acid. The production medium is inoculated with 600 ml of the above-prepared propagation culture. Fermentor conditions are as follows:

| pH: | 6.5; |
|---|---|
| Temperature: | 29° C.; |
| Aeration: | 1.7 v/v/m; and |
| Agitation: | 370 rpm. |

After about 24 hours of biomass development period, decanoic acid feeding is commenced at a rate of 1.2 grams/hour/liter.

The feed rate range is altered according to the response of dissolved oxygen (DO) measured by a membrane electrode as described in Example I, supra. 3 Kg of mineral oil (Amoco Oil Company SUPERLA® White Mineral Oil #5) and 20 grams of 10% antifoam (MAZU DF 100) are also added when the acid substrate feeding is commenced. When the gamma-decalactone level in the oil phase is above 10 grams/kilograms of oil phase, the oil phase is exchanged with 4 kg of fresh mineral oil. After biotransformation of the substrate, the two mineral oil phases are combined and then treated for decanoic acid removal. The resulting product is then distilled to yield a crude gamma-decalactone product as described in Example I, supra. A total of recovered oil distillate is 88 grams. The purity of gamma-decalactone in the crude oil phase of distillate is 90.1%.

EXAMPLE III

Production of Gamma-decalactone in 20 Liter Fermentors using various Nitrogen Sources Reactions:

The medium of seed and propagation flasks are prepared, inoculated and incubated in the same manner as set forth in Example I, supra.

12 Liters of production medium in 20 liter fermentors are produced using different nitrogen sources (1.0%), TASTONE® 900 (0.5%), TWEEN® 80 (0.05%), 10% antifoam (MAZU DF 100) (0.5%) and glucose (2.0%). Fermentor conditions are as follows:

| | |
|---|---|
| pH: | 6.5; |
| Temperature: | 29° C.; |
| Aeration: | 1.7 v/v/m; and |
| Agitation: | 370 rpm. |

The results of the gamma-decalactone yields using the different nitrogen sources are set forth in Table I below and indicated as Examples III-1, III-2, III-3, III-4, III-5 and III-6.

TABLE I

GAMMA-DECALACTONE PRODUCTION USING VARIOUS NITROGEN SOURCES IN 20 LITER FERMENTOR

| Example | Nitrogen Source | Gamma-Decalactone Yield |
|---|---|---|
| III-1 | Soy Peptone 50 M | 78.6 grams |
| III-2 | Soy Peptone 50 KM | 15.3 grams |
| III-3 | Yeast Extract 1003 | 13.6 grams |
| III-4 | HY SOY J ® | 73.7 grams |
| III-5 | TASTONE ® 154 | 98.1 grams |

TABLE I-continued

GAMMA-DECALACTONE PRODUCTION USING VARIOUS NITROGEN SOURCES IN 20 LITER FERMENTOR

| Example | Nitrogen Source | Gamma-Decalactone Yield |
|---|---|---|
| III-6 | Bactopeptone | 72.0 grams |

EXAMPLE IV

Production of Gamma-decalactone in 20 Liter Fermentors using various Mineral Oil Concentrations Reactions:

The medium of seed and propagation flasks are prepared, inoculated and incubated in the same manner as is set forth in Example I, supra. 12 Liters of production medium in 20 liter fermentors are produced with yeast extract (1.5%), TWEEN® 80 (0.05%), 10% antifoam (MAZU DF 100) (0.5%) and glucose (2.0%). The decanoic acid is fed after 24 hours of initial growth of *Mortierella isabellina* IFO 7873 and mineral oil (Amoco Oil Company SUPERLA® White Mineral Oil #5) is added at different concentrations as set forth below after 3 hours of carboxylic acid feed as is set forth in Table II below for Examples IV-1, IV-2 and IV-3.

TABLE II

GAMMA-DECALACTONE PRODUCTION USING VARIOUS MINERAL OIL CONCENTRATIONS IN A 20 LITER FERMENTOR

| Example | Mineral Oil (%)* | Gamma-Decalactone Yield |
|---|---|---|
| IV-1 | 0 | 15.2 grams |
| IV-2 | 35 | 78.9 grams |
| IV-3 | 50 | 74.4 grams |

*Percentage of total fermentor volume.

EXAMPLE V

Production of Gamma-dodecalactone in 20 Liter Fermentors

Reactions:

The medium of seed and propagation flasks are prepared, inoculated and incubated in the same manner as is set forth in Example I, supra. The medium of seed flasks consists of bactopeptone (1.0%), yeast extract (0.5%), TWEEN® 80 (0.05%) and glucose (5.0%). The medium pH is adjusted to 4.5 using 85% phosphoric acid and the seed flasks containing 200 ml of medium are autoclaved for 30 minutes at 121° C. The seed flask is inoculated with one PDA slant. The seed flasks are incubated at 33° C., 120 rpm for 3 days.

The production medium of the 20 liter fermentor consists of yeast extract (1.5%), TWEEN® 80 (0.05%), 10% antifoam (MAZU DF 100) (0.5%) and glucose (2.0%). The ingredients are measured based on a 10 liter working volume of the fermentor. 500 Ml of sterile 50% glucose is added after sterilization. The production medium is inoculated with 600 ml of the seed inoculum. Initial fermentor conditions are as follows:

| pH: | no control for the initial 18 hours; |
|---|---|
| Temperature: | 30° C.; |
| Aeration: | 1.7 v/v/m; and |
| Agitation: | 370 rpm. |

After 18 hours, the temperature of the fermentor is slowly raised to 38° C. over a one hour period and the pH is also slowly raised to 6.5 using a 45% aqueous sodium hydroxide solution. When *Mortierella isabellina* IFO 7873 is fully grown after 22 hours, the feeding of the dodecanoic acid and mineral oil (Amoco Oil Company SUPERLA® White Mineral Oil #5) mixture (1:9 weight:weight ratio) at 50° C. is initiated at a rate of 0.8 grams of dodecanoic acid/hour/liter, which is changed on a continual basis using the response of dissolved oxygen (DO) measured by a membrane electrode. Thus, for example, in the event that the DO increases suddenly, the acid feeding is ceased; but feeding is resumed whenever the DO drops gradually or stays constant for a period of 0.5 hours. 2.5 Kilograms of mineral oil and 20 grams of 10% antifoam (MAZU DF 100) are added immediately prior to the commencement of feeding of dodecanoic acid. The DO increases gradually as the dodecanoic acid is fed over a period of 24 hours. Gamma-dodecalactone and dodecanoic acid levels in the oil and aqueous phases are also monitored using GC analysis every hour. At the end of the biotransformation, the broth pH is adjusted to between 2 and 4 using citric acid. An equal volume of 30% sodium chloride is then added to the fermentor. The resulting mixture is then heated to 100° C. and maintained at 100° C. for a period of 15 minutes. The dodecanoic acid is now contained in the mineral oil phase. The dodecanoic acid in the mineral oil phase is removed using the method set forth in Example I, supra. The gamma-dodecalactone is then recovered from the oil phase using rushover distillation (135° C. at 0.1 mm/Hg pressure). A total of 40.56 grams of gamma-dodecalactone is recovered from the fermentor and the gamma-dodecalactone yield is 4.1 grams/liter of liquid medium.

The invention being thus described, it will be obvious that the same may be varied in several manners. Such variations are not to be regarded as a departure from the spirit and scope of the invention and all such modifications are intended to be included within the scope of the following claims:

What is claimed is:

1. A process for preparing a composition containing a significant amount of at least one $C_{10}$ and/or $C_{12}$ lactone defined according to the structure:

wherein N is an integer of 1 or 2 comprising the sequential steps of:

(i) carrying out a fermentation of a $C_{10}$ and/or $C_{12}$ carboxylic acid defined according to the structure:

wherein N is an integer of 1 or 2 in the presence of an organism selected from the group consisting of:

*Mortierella isabellina*, ATCC 44583;
*Mortierella isabellina*, ATCC 38063;
*Mortierella isabellina*, CBS 221.29;
*Mortierella isabellina*, IFO 7873;
*Mortierella isabellina*, IFO 7884; and
*Mortierella ramanniana* var. *angulispora*, IFO 81870 in aqueous media and in the presence of mineral oil having a specific gravity of from 0.830 up to 0.905 at 60° F. and a viscosity of from 50 up to 400 Sayboldt Seconds at 100° F., said mineral oil being a mixture of liquid $C_{15}$–$C_{50}$ saturated hydrocarbons, at a pH in the range of from about 3 up to about 9, at a temperature in the range of from about 15° C., for a period of from about 10 hours up to about 150 hours, under aerobic conditions with the range of feed rate of $C_{10}$ and/or $C_{12}$ carboxylic acid being from 0.1 up to 100 grams/hour/liter and an aeration rate of from about 0.3 up to about 3.0 v/v/m and with said mineral oil being present in an amount of from 1% up to 80% by volume of the total fermentor contents volume whereby a hydroxycarboxylic acid defined according to the structure:

is produced wherein N is an integer of 1 or 2, according to the reaction:

(ii) effecting lactonization of the resulting $C_{10}$ and/or $C_{12}$ hydroxycarboxylic acid to form at least one lactone defined according to the structure:

according to the reaction:

wherein N is an integer of 1 or 2; and (iii) distilling the resulting reaction product in order to recover at least one of said $C_{10}$ and/or $C_{12}$ lactone compounds defined according to the structure:

2. The process of claim 1 wherein N=2 and the acid substrate is dodecanoic acid and the reaction product is gamma-dodecalactone.

3. The process of claim 1 wherein N=1, the acid substrate is decanoic acid and the product is gamma-decalactone.

4. The process of claim 1 wherein the acid substrate is a mixture of decanoic and dodecanoic acids and the reaction product is mixture of gamma-decalactone and gamma-dodecalactone.

5. The process of claim 1 wherein the acid substrate is one or a mixture of hydrolyzates of vegetable oils which contain substantial quantities of decanoic acid and the reaction product is gamma-decalactone.

6. The process of claim 1 wherein the acid substrate is one or a mixture of hydrolyzates of vegetable oils which contains substantial quantities of dodecanoic acid and the product is gamma-dodecalactone.

7. The process of claim 1 wherein the acid substrate is one of or a mixture of vegetable oils in admixture with lipase, wherein said acid substrate contains substantial quantities of both decanoic and dodecanoic acids and the reaction product is a mixture of gamma-decalactone and gamma-dodecalactone.

8. The process of claim 1 wherein the organism used is *Mortierella isabellina*, IFO 7873.

9. The process of claim 2 wherein the organism used is *Mortierella isabellina*, IFO 7873.

10. The process of claim 3 wherein the organism used is *Mortierella isabellina*, IFO 7873.

11. The process of claim 4 wherein the organism used is *Mortierella isabellina*, IFO 7873.

12. The process of claim 5 wherein the organism used is *Mortierella isabellina*, IFO 7873.

13. The process of claim 6 wherein the organism used is *Mortierella isabellina*, IFO 7873.

14. The process of claim 7 wherein the organism used is *Mortierella isabellina*, IFO 7873.

* * * * *